United States Patent [19]

Kurtz et al.

[11] 4,445,884
[45] May 1, 1984

[54] AIR PURGE UNIT FOR AUTO TRANSFUSION APPARATUS

[75] Inventors: Leonard D. Kurtz, Woodmere; Joseph LiCausi, Port Jefferson Station, both of, NY

[73] Assignee: BioResearch Inc., Farmingdale, N.Y.

[21] Appl. No.: 292,425

[22] Filed: Aug. 14, 1981

[51] Int. Cl.³ .................. A61M 37/00; A61M 1/00
[52] U.S. Cl. ................................ 604/4; 604/317; 55/159
[58] Field of Search ............ 137/205; 128/276, 214 R, 128/214.4; 55/159, 38 SC, 417, 420, 432; 604/4, 5, 6, 252, 122, 317, 319

[56] References Cited

U.S. PATENT DOCUMENTS

| | | | |
|---|---|---|---|
| 3,859,998 | 1/1975 | Thomas | 128/214.4 |
| 3,901,808 | 8/1975 | Bokros | 604/4 |
| 3,929,130 | 12/1975 | Hargest | 604/5 |
| 3,964,479 | 6/1976 | Boag et al. | 604/5 |
| 4,046,144 | 9/1977 | McFarlane | 128/214.4 |

OTHER PUBLICATIONS

Catalog Cut "Gore-Tex Membrane Products", W. L. Gore and Assoc., Elkton, Md. 21921.

*Primary Examiner*—C. Fred Rosenbaum
*Assistant Examiner*—J. L. Kruter
*Attorney, Agent, or Firm*—Larson and Taylor

[57] ABSTRACT

An air purge unit for an auto transfusion device is provided wherein a housing having a passageway therein is mounted on the top wall of a blood collection chamber. A filter having pore sizes smaller than the size of red blood cells is disposed within said passgeway together with an umbrella valve and a oneway flap valve which will permit the passage of air from within the collection chamber through the valves to a source of suction or to atmosphere. When the air is purged from the interior of the collection chamber, the red blood cells will block the filter and prevent the further passage of fluid therethrough.

6 Claims, 5 Drawing Figures

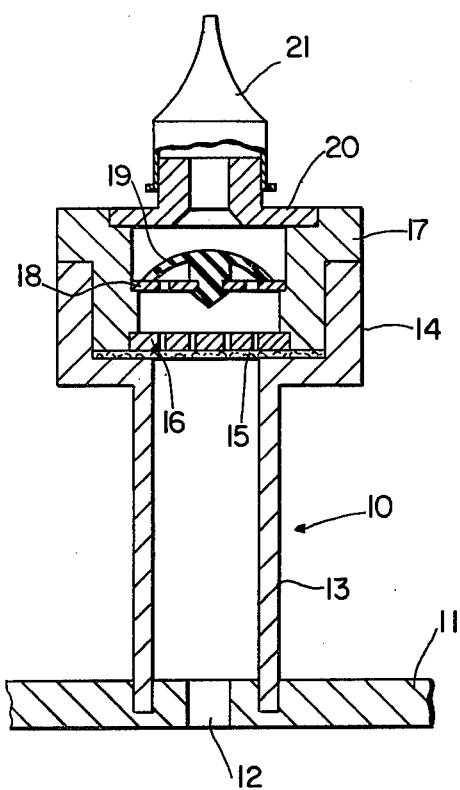
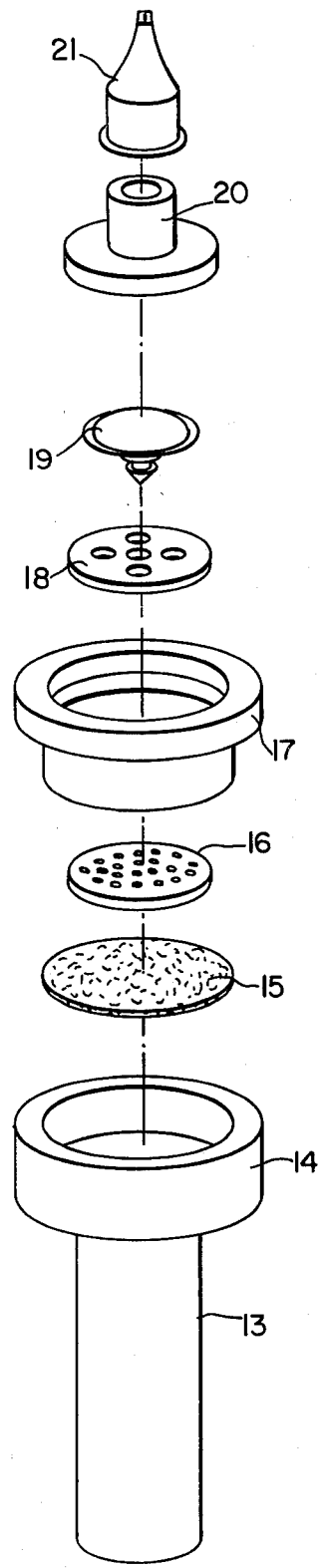
FIG. 2
FIG. 3

AIR PURGE UNIT FOR AUTO TRANSFUSION APPARATUS

FIELD OF THE INVENTION

This invention relates generally to an auto transfusion device and more specifically to an air purge unit for a disposable auto transfusion device which is adapted to be mounted on the collection chamber for blood. The present invention is a continuation-in-part of a copending application for disposable auto transfusion device filed Aug. 5, 1981 Ser. No. 290,666.

BACKGROUND OF THE INVENTION

During certain types of surgery, particularly in connection with chest cavity surgery, the patient frequently loses large amounts of blood. Ordinarily, the lost blood is aspirated away and the patient is given a transfusion of donated blood to make up for the lost blood. An alternative arrangement is to provide an auto transfusion device which will collect the blood lost by the patient and transfuse this blood into the patient's circulatory system. Such an apparatus is disclosed in our copending application referred to hereinbefore.

There are disclosed in the prior art various systems for auto transfusion. For example, in U.S. Pat. No. 3,191,600 (Everett) an auto transfusion apparatus is disclosed which includes a vacuum source and a plurality of suction tips for immersion in pools of blood. The blood is collected in a collection chamber and is returned to the patient through a oneway valve. Another auto transfusion device is disclosed in U.S. Pat. No. 3,492,991 (Dyer) and includes a container equipped with a filter through which the blood is gravity fed back to the patient. In U.S. Pat. No. 3,993,067 (Schachet et al) an auto transfusion device is disclosed in which the blood is forced back into the patient by pressure in the collection chamber. Still another auto transfusion device is disclosed in U.S. Pat. No. 4,047,526 (Reynolds et al). This patent discloses a collection chamber in which blood is continuously aspirated. A blood bag with an outwardly urged spring is connected to the collection chamber to withdraw some of the blood therefrom. The blood collected in the blood bag is then later reintroduced into the patient. There has also been disclosed in the prior art a spring operated device which forces blood from a blood bag into the patient. Such a device is disclosed in U.S. Pat. No. 3,565,292 (Jinotti).

While auto transfusion has been disclosed in the prior art, there is a need for an air purge unit which will effectively prevent the possibility of air being reintroduced into the patient's circulatory system which could lead to disastrous consequences. According to the present invention, an air purge unit is provided which ensures that all air within the collection chamber for the blood is eliminated before the blood is reintroduced into the patient's circulatory system.

SUMMARY OF THE INVENTION

In accordance with the present invention, an air purge unit is provided which is adapted to be mounted on the top wall of a collection chamber for blood in an auto transfusion apparatus such as disclosed in our prior patent application, filed Aug. 5, 1981.

The air purge unit comprises a housing having a passageway therethrough with the inner end of the passageway being in fluid communication with the interior of the collection chamber. There is provided a filter within the passageway which has a pore size smaller than the diameter of red blood cells. Thus, this filter will pass any fluids having particles of a size smaller than the pore size of the filter, but will not permit red blood cells to pass therethrough. Adjacent the filter within the passageway there is provided an umbrella type valve which will open to permit air or fluids to pass therethrough but, which will prevent the admission of outside air from entering the interior of the collection chamber. On the outlet from the housing is a flap valve which is also a oneway valve and also serves to ensure that no atmospheric air can enter the air purge unit.

In use, a tube connects the air purge unit with a source of regulated suction so that any air which is drawn into the collection chamber is withdrawn through the purge unit. As more fully disclosed in applicants' copending application, when the collection chamber is filled with blood the collection chamber is put under pressure so as to force any air remaining within the collection chamber out through the air purge unit. When the passage way between the filter and the interior of the collection chamber is filled with blood, the red blood cells clog the filter to block the filter to prevent the loss of blood therethrough. Thus, all air within the collection chamber is removed and the possibility of an air emboli within the patient's circulatory system is virtually eliminated.

Other features and advantages of the present invention are stated or are apparent from the detailed description of a presently preferred embodiment of the invention found hereinbelow.

BRIEF DESCRIPTION OF THE DRAWINGS

FIG. 2 is a cross-sectional view of the air purge unit, FIG. 3 is an exploded view of the parts of the air purge unit shown in FIG. 2.

DETAILED DESCRIPTION OF THE PREFERRED EMBODIMENT

Figure 1:
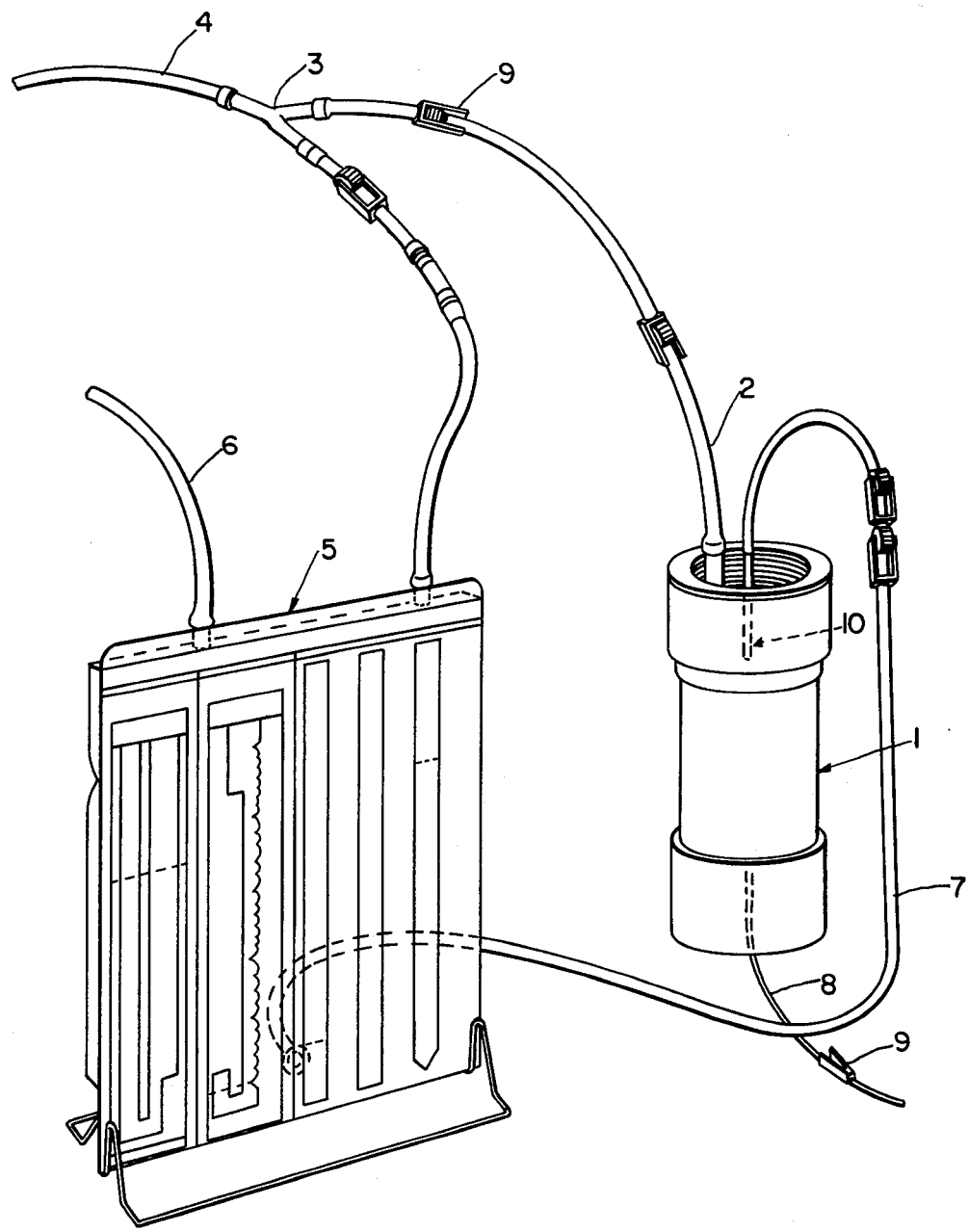
FIG. 1 is a perspective view showing an auto transfusion system with an air purge unit according to the present invention installed on the collection chamber.

With reference now to the drawings in which like numerals represent like parts thorughout the several views, a perspective view of the auto transfusion system is shown in FIG. 1 wherein there is shown at 1 a collection chamber for blood. This collection chamber is disclosed in detail in copending application, filed Aug. 5, 1981 Ser. No. 290,666, entitled "Disposable Auto Transfusion Device". The inlet to the collection chamber is shown at 2 and connects through a Y connector 3 with a tube 4, the free end of which is disposed in a patient's body cavity to collect blood therefrom. A three chambered drainage apparatus is shown at 5, this device being similar to the underwater drainage device disclosed in U.S. Pat. Nos. 3,363,626 and 3,363,627. Such an underwater drainage device will maintain any degree of suction in accordance with the setting in the manometer chamber in the device. The tube 6 extending form the underwater drainage device is connected with a source of suction. A tube 7 extends from an outlet in the upper end of the collection chamber and is connected with theunderwater drainage device so that the regulated negativity maintained by the underwater drainage device passed through the tube 7 into the interior to the collection chamber 1.

An outlet 8 extends from the bottom wall of the collection chamber. Clamps such as shown at 9 are located on tubes 2, 7 and 8. As described in the copending application hereinbefore referred to, the device is operated by applying suction through tube 6 so as to aspirate blood through the tubes 4 and 2 into the collection chamber. Air which is within the collection chamber is drawn out through tube 7. When the collection chamber is filled with blood, the locking clamp on tube 2 is closed and the spring mechanism on the collection chamber is released so as to force the top wall of the chamber downwardly in the manner described in the hereinbefore referred to copending patent application. Any air remaining within the upper end of the collection chamber is forced out through tube 7. Upon completion of the air purge from the collection chamber, the locking clamp on tube 7 is closed and the clamp on tube 8 is opened so that blood is forced outwardly through the tube 8 into the circulatory system of the patient.

The air purge unit according to the present invention is disposed as shown at 10 in FIG. 1 and is connected with the tube 7 so as to be disposed within the pathway between the interior of the collection chamber and the suction source. The top wall 11 of the collection chamber is shown in FIG. 2 as having an outlet aperture 12 disposed therein. Outlet aperture 12 forms the inlet of the air purge unit 10. The air purge unit 10 is located on the top wall and comprises a housing 13 with a passageway extending therethrough and having a flanged upper end portion as shown at 14. Seated on the horizontal outwardly extending surface of the flange 14 is a filter element 15. This filter element has a pore size of approximately two microns so that air may readily diffuse through this filter. Disposed on the upper surface of the filter is a spacer element 16 having a plurality of apertures therein. The filter and spacer are held in position by means of a valve seat housing 17 which is press fit within the outer flange portion 14 of housing element 13. Seated within member 17 is an umbrella type apertured valve seat 18 having a oneway resilient umbrella valve 19 mounted thereon. An apertured plug insert 20 is seated within a recess in the upper end of the valve seat housing 17 and a resilient oneway flap valve 21 is fitted over the outer surface of the plug insert 20.

The filter 15 having a pore size of two microns will permit any air within the collection chamber to pass therethrough but will not pass red blood cells which have a size of approximately seven microns. Thus, when the passageway beneath the filter 15 becomes filled with blood, the filter prevents passage of the blood therethrough, thus blocking the air purge unit.

The oneway valve 19 and 21 ensure that no air can pass from the exterior of the unit into the collection chamber. Thus, even in the event the tube 7 becomes disconnected from the underwater drainage device or the drainage device does not function properly so that the tube 7 becomes exposed to atmospheric air, no air will be admitted into the collection chamber.

Figure 4:
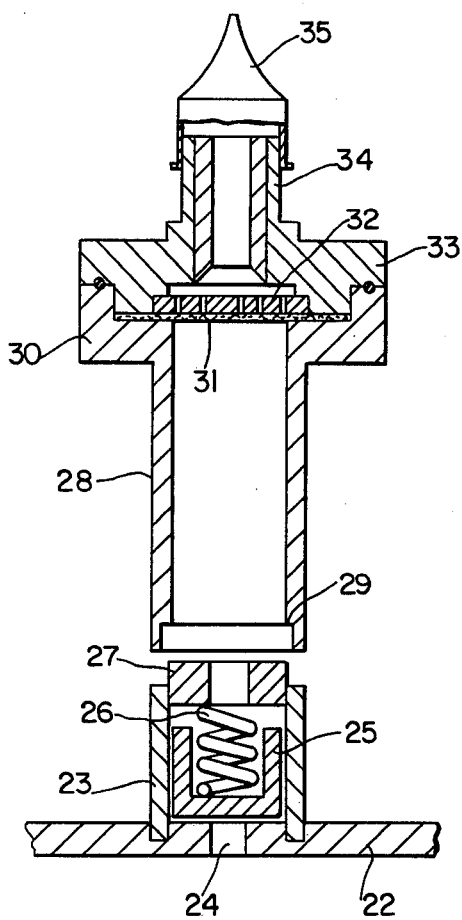
FIG. 4 is a cross-sectional view of a modified form of air purge unit.
Figure 5:
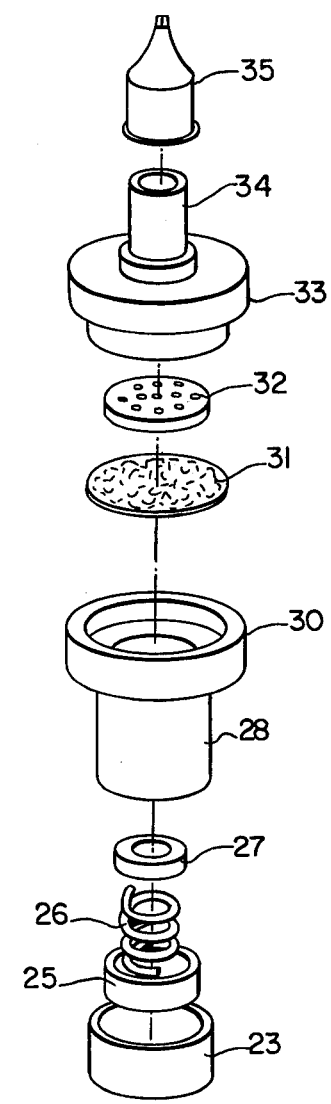
FIG. 5 is an exploded view of the parts of the air purge unit shown in FIG. 4.

In FIGS. 4 and 5 there is shown a modified form of air purge unit. In this embodiment the blood bag cover 22 has a separate passageway (not shown) for connection with the suction device. The unit comprises a hollow ring shaped base 23 which is secured to the top of the blood bag cover and surrounds the opening 24.

Disposed within the base 23 is a spring housing 25 which also serves as a valve element for closing opening 24 as will appear more clearly hereinafter. A compression spring 26 is disposed within the housing 25 and acts between the housing 25 and an apertured retaining ring 27.

A lower housing member 28 of clear plastic is secured to the base 23 and an inner flange 29 forms a seat for the retaining ring 27. It can be seen that the compression spring 26 will force the retaining ring 27 and spring housing 25 apart so that normally the ring is seated on the flange 29 and the end of the housing is seated firmly against the top of the blood bag cover, thus closing the opening 24.

The upper end of the housing 28 has an outwardly extending peripheral flange portion 30 which forms a seat for a filter element 31. This filter element is similar to the element 15 of the FIGS. 1 to 3 embodiment and has a pore size of less than 7 microns so as to pass particles of a smaller size but to block the passage of red blood particles having a pore size of seven microns. A vented spacer support for the filter is shown at 32 which seats in a circular recess formed in the top cover 33 of the unit. The top cover is press fit within the flanged portions of lower housing member 28 so as to firmly seat the vented spacer support 32 and filter element 31.

An outlet port 34 formed in the top cover 33 is closed by a one way flap valve 35 of the Hemlich type comprising a pair of resilient elements having a slit therebetween and normally urged together. Upon internal pressure in excess of the force holding the resilient elements together the flap valves will open and permit the passage of fluids therebetween.

In operation the spring pressed valve 25 and the flap valve 35 normally remain closed during the filling of the blood bag. After the blood bag is filled to the extent desired, the spring mechanism described in the copending application filed on Aug. 5, 1981, is released applying pressure to the contents of the bag. The internal pressure exceeds 50 millimeters of mercury and the spring valve 25 is forced open to pass air and liquid there through. The filter 31 will permit the passage of air therethrough as well as any particles of less than seven micron size. The flap valve 35 will open to permit the passage of air therethrough. When the filter 31 becomes clogged with red blood cells it prevents the passage of blood therethrough. The attending physician can readily determine that the air purge unit is operative by viewing the blood filled housing element 28.

Thus, while the invention has been described in detail with respect to an exemplary embodiment thereof, it will be understood by those of ordinary skill in the art that these and other variations and modifications may be effected in the exemplary embodiment within the scope and spirit of the invention.

We claim:

1. In an autotransfusion apparatus, a collection chamber for blood, an air purge means directly mounted on said collection chamber for purging the air within the collection chamber when blood and air within the collection chamber is put under positive pressure said air purge means comprising a housing, a passageway in said housing in fluid communication with the interior of said collection chamber and having an outlet, a filter disposed in said passageway, said filter having a pore size smaller than the size of red blood cells, a oneway valve disposed in said passageway in series with the filter between said filter and said outlet, said oneway valve permitting air to pass therethrough from the interior of said collection chamber and preventing air from entering said collection chamber, said filter permitting air to pass therethrough until blood fills said passageway between the interior of said collection chamber and the filter.

2. In an apparatus according to claim 1 wherein said filter has a pore size less than seven microns.

3. In an apparatus according to claim 2 wherein both an umbrella valve and a oneway flap valve are disposed in series in said housing.

4. In an apparatus according to claim 2 and further including a vented spacer disposed on one face of said filter.

5. In an apparatus according to claim 1 wherein said oneway valve includes an umbrella valve and flap valve disposed in series in said passageway.

6. In an apparatus according to claim 1 and further including a spring valve normally closing said passageway and opening in response to pressure from air within the collection chamber.

* * * * *